United States Patent [19]

Carder

[11] Patent Number: 4,961,047

[45] Date of Patent: Oct. 2, 1990

[54] ELECTRICAL POWER CONTROL APPARATUS AND METHODS

[75] Inventor: Timothy J. Carder, Brighton, England

[73] Assignee: Smiths Industries Public Limited Company, London, England

[21] Appl. No.: 427,214

[22] Filed: Oct. 24, 1989

[30] Foreign Application Priority Data

Nov. 10, 1988 [GB] United Kingdom ................. 8826316
Jul. 18, 1989 [GB] United Kingdom ................. 8916360

[51] Int. Cl.$^5$ .......................... A61B 17/39; G05F 1/66
[52] U.S. Cl. .................................... 323/322; 323/911; 128/908; 606/35; 606/42
[58] Field of Search ............... 323/241, 318, 322, 911; 363/96, 97; 128/908; 606/35, 37, 38, 42, 47, 48

[56] References Cited

U.S. PATENT DOCUMENTS

| | | | |
|---|---|---|---|
| 3,952,748 | 4/1976 | Kaliher et al. | 323/911 |
| 4,416,277 | 11/1983 | Newton et al. | 606/35 |
| 4,498,475 | 2/1985 | Schneiderman | 323/911 |
| 4,848,335 | 7/1989 | Manes | 128/908 |
| 4,862,889 | 9/1989 | Feucht | 128/908 |

FOREIGN PATENT DOCUMENTS

| | | |
|---|---|---|
| 0136855 | 4/1985 | European Pat. Off. . |
| 8605604 | 9/1986 | PCT Int'l Appl. . |
| 2155707 | 9/1985 | United Kingdom . |
| 2164473 | 3/1986 | United Kingdom . |

*Primary Examiner*—Peter S. Wong
*Attorney, Agent, or Firm*—Pollock, Vande Sande & Priddy

[57] ABSTRACT

Electrosurgery apparatus includes an r.f. power amplifier with an output to a patient electrode. The amplifier is controlled by the voltage of input signals from a control unit which receives a sample of the voltage and current of the output signal. The voltage and current signals are supplied to A/D converters to provide two digital signals that are used to address a look-up table in an EPROM and provide a digital output representative of impedance. A switch is set by the user to the desired mode/power curve and this provides a digital signal which together with the impedance signal is used to address a second look-up table in an EPROM which contains digital representations of the required output voltage of the amplifier to produce the desired power level. An adder compares the required voltage with a feedback of the actual voltage to produce an error signal that is supplied to the amplifier to control its output.

11 Claims, 3 Drawing Sheets

ELECTRICAL POWER CONTROL APPARATUS AND METHODS

BACKGROUND OF THE INVENTION

This invention relates to electrical power control apparatus and methods.

The invention is more particularly, but not exclusively, concerned with controlling the power of electrosurgery apparatus.

Electrosurgery, such as diathermy, units are often used during surgery such as to cut tissue and coagulate blood vessels. Radio frequency current is supplied via a hand-held electrode that is applied to the surgical site and a return path is provided from the patient by means of a large area electrode fixed to some other part of the patient's body. In order to provide safe efficient operation it is necessary to control the power delivered to the patient as the load impedance changes. In this respect, the load impedance will vary according to the area of the hand-held electrode that contacts the tissue and according to the nature of the tissue contacted. The power level also needs to be adjustable by the surgeon according to the surgical process in which the apparatus is being used.

At present, this control of power is achieved by means of feedback from the output, by analog processing and by pre-set current and voltage limits. The present techniques suffer from the difficulty that it is not readily possible to vary the power curves of the apparatus, that is, the way in which power varies with impedance, according to different functions that the apparatus may need to perform and according to the front panel settings made by the user. It may be desirable to be able to vary the shape of the power curves at different power level settings but this is not readily achievable with existing apparatus. It is also difficult to compensate for non-linearity in the analog processing which would give rise to deviations from the desired power curves.

BRIEF SUMMARY OF THE INVENTION

It is an object of the present invention to provide electrical power control apparatus and methods that can be used to alleviate these difficulties.

According to one aspect of the present invention there is provided electrical power control apparatus including a power supply unit arranged to deliver an alternating power output signal at a level that is controlled by an input signal to the power supply unit, means for deriving a first digital signal representative of the voltage and current of the output signal, means for deriving a second digital signal representative of a performance characteristic of the apparatus, store means including a plurality of storage locations each of which contains information for use in providing the input signal, the first and second digital signals together defining the location of one of the storage locations such that as the output voltage, current or performance characteristic changes a different one of the storage locations is addressed and the input signal is varied accordingly to control the output signal.

The performance characteristic is preferably set by means of a manually settable switch. The first digital signal is preferably an impedance signal. The apparatus preferably includes second store means including a plurality of storage locations each of which contains information representative of the impedance signal, the storage locations in the second store being addressed by a digital signal representative of the voltage of the output signal and a digital signal representative of the current of the output signal. The second digital signal may be representative of the shape of the desired curve of power against impedance.

The apparatus may include comparator means arranged to compare an output signal from the store means with a feedback signal from the output signal of the power supply, the input to the power supply unit being derived by the comparator means. The comparator means may provide an input to alarm means, the alarm means being arranged to provide an alarm signal when the output of the comparator means exceeds a predetermined amount. The feedback signal may be a voltage signal and, or alternatively, a power signal. The apparatus may include a manually settable power level switch, the input signal to the power supply unit being adjustable according to the desired power level as indicated by the power level switch. The storage locations in the store means may contain representations of the input signal at full power, representations at full power being modified according to the desired power level as indicated by the power level switch. The apparatus may include means for deriving a third digital signal representative of time, the first, second and third digital signals together defining the location of one of the storage locations. The store means is preferably an EPROM. The alternating power output signal may be at radio frequency.

According to another aspect of the present invention there is provided electrosurgery apparatus including electrical power control apparatus according to the above one aspect of the invention in which the power supply unit provides a radio frequency output, and a patient electrode connected to receive the radio frequency power output signal from the power supply unit.

According to a further aspect of the present invention there is provided a method of controlling the electrical power delivered by a power supply unit of the kind that produces an alternating power output signal, including the steps of: deriving a first digital signal representative of the voltage and current of the output signal, deriving a second digital signal representative of a performance characteristic, supplying the first and second digital signals to identify one of a plurality of storage locations in store means, reading out from said storage location information contained therein and supplying a signal derived from said information to said power supply unit in such a way as to control the output of said power control.

The information contained in the storage locations may be compared with information derived from the output of the power supply unit, the output of the power supply unit being controlled in accordance with the comparison.

Electrosurgical apparatus and its method of operation, in accordance with the present invention, will now be described, by way of example, with reference to the accompanying drawings.

DETAILED DESCRIPTION OF THE PREFERRED EMBODIMENT

Figure 1:
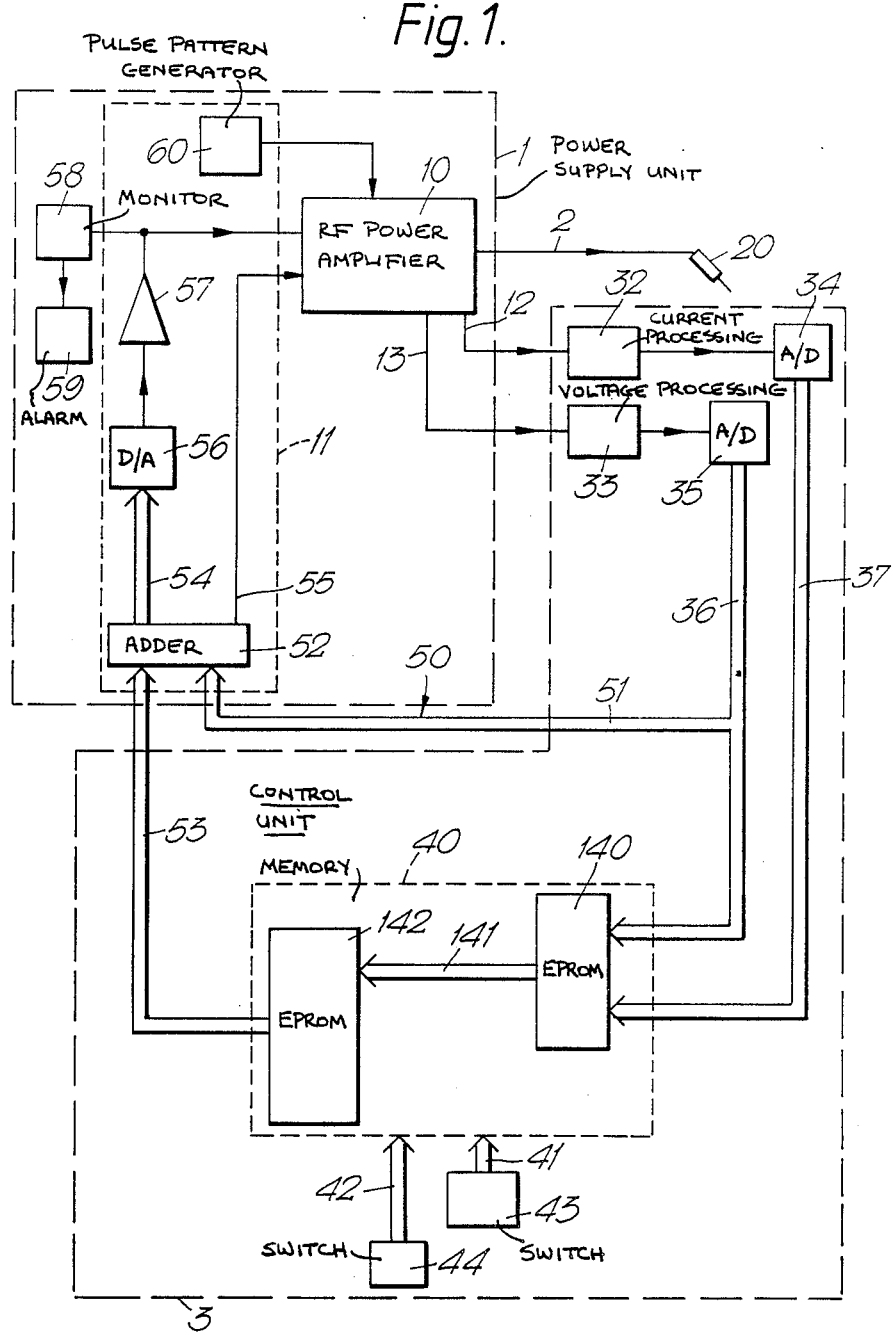
FIG. 1 shows the apparatus schematically.

With reference first to FIG. 1, the apparatus includes a power supply unit 1 that provides an electro surgical, radio frequency output signal on line 2 to an active, patient electrode 20 under control of a control unit 3.

The power supply unit 1 includes a radio frequency power amplifier 10 the output of which is controlled by a power control unit 11. The power control unit 11 receives two voltage input signals on lines 51 and 53 from the control unit 3 and varies the power level of the output of the amplifier 10 according to the difference in their magnitudes.

The power amplifier 10 also provides two output sample signals on lines 12 and 13 which are supplied to a current processing unit 32 and a voltage processing unit 33 in the control unit 3. The analog outputs of the voltage and current processing units 32 and 33 are supplied to respective analog-to-digital converters 34 and 35 which provide two five-bit output digital signals on lines 36 and 37 representative of the voltage and current respectively of the power output signal. The signals on lines 36 and 37 are supplied to a memory 40, a sample of the voltage signal on line 36 also being supplied to the power control unit 11 via line 51. The memory 40 includes a 64kByte EPROM 140 which contains a look-up table of impedance and which is addressed by the voltage and current values on lines 36 and 37 to provide an eight-bit digital output signal on line 141 representative of impedance. Alternative arrangements could be used to derive an indication of impedance, such as, for example, by dividing the voltage by the current signal. This could be done by dividing the analog voltage signal by the analog current signal to produce an impedance signal that is subsequently converted to digital form. The impedance signal derived from the EPROM 140 is used to address a second look-up table in a 64kByte EPROM 142 or similar programmable memory.

The memory 40 is also connected to receive another set of digital signals on lines 41 and 42 which extend to two manually settable switches 43 and 44 on the front panel of the apparatus. One switch 43 is set according to the desired power level and this produces a five-bit digital signal on line 41 to the memory 40. The switch 43 may be of the binary kind or be analog and include an analog-to-digital converter. The other switch 44 is set according to the electro-surgical mode/power curve desired by the user, that is, for example cut, coagulate, fulgurate, or blend and produces a two-bit digital signal on line 42 to the memory 40. Alternatively, or additionally, the switch 44 may be set to coloscopy, arthroscopy, trans-urethral resection or the like. Where selection is required between more than four modes it is, of course, necessary to produce a digital signal of more than two bits. The signals on lines 41 and 42 are therefore representative of the desired performance characteristic of the apparatus.

Figure 3:
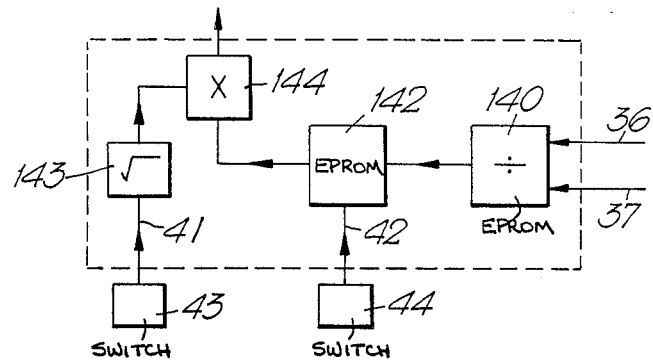
FIG. 3 illustrates a part of the apparatus.

The operation of the memory 40 is illustrated in FIG. 3 which shows the voltage and current inputs on lines 36 and 37 being converted into an impedance signal by the look-up table in the EPROM 140. This impedance signal is used to address the other look-up table in the EPROM 142 in conjunction with a signal from the mode/power curve switch 44. This look-up table in EPROM 142 contains eight-bit representations of the voltage required to produce the desired power output at the present impedance for the particular power curve selected and at a full power setting. This is then multiplied with an input derived from the power level control switch 43 to produce the voltage required at the desired power setting. The square root of the power level setting is taken at 143 before multiplying it at 144 by the required full power voltage.

Figure 2:
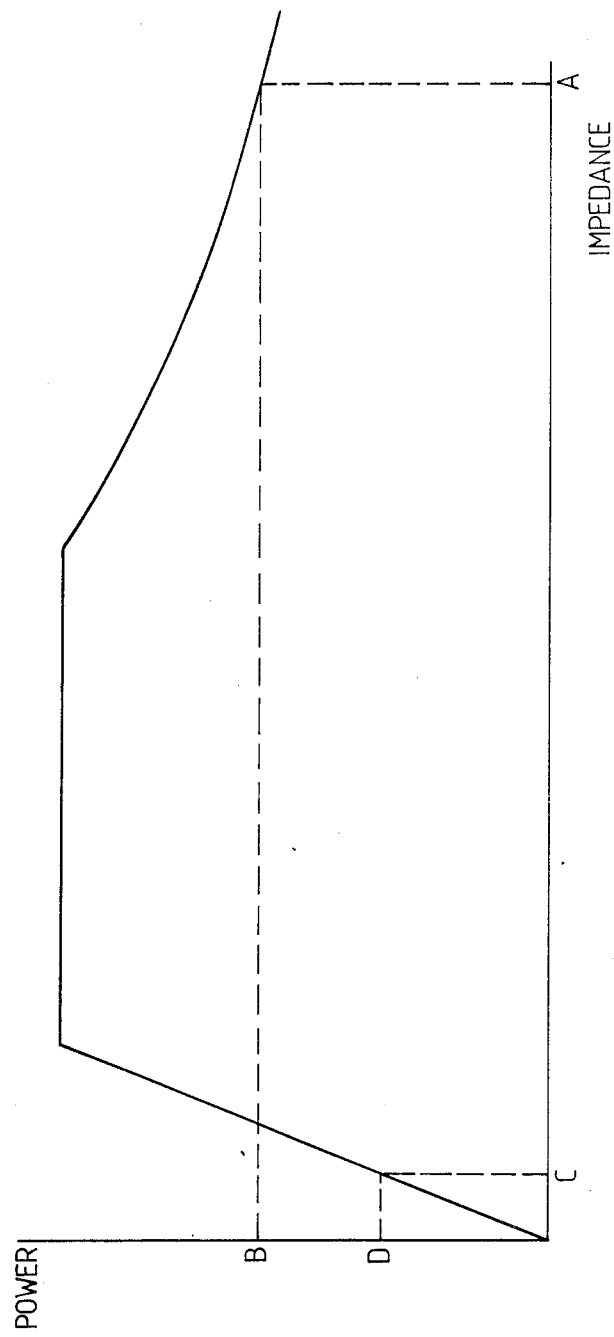
FIG. 2 is a graph illustrating operation of the apparatus.

The information stored at each location in the EPROM 142 is pre-calculated, such as by use of a suitable computer program, taking into the account the shape of the power curve and the damping factor (that is, the time taken to reach the required power level, for example, when changing from open circuit to a predetermined load impedance). One example of a power curve is shown in FIG. 2. This shows the relationship between power and load impedance at one particular power level setting. It will be appreciated that a whole family of curves will be produced for different power level settings and the shape of the curve will differ according to whether the apparatus is to be used, for example, in the cut, coagulation, blend or fulgurate mode.

In use, the surgeon sets the switches 43 and 44 as desired according to the power level and mode. When the unit is initially turned on, and before the hand-held, active electrode 20 is brought into contact with the patient, there will be a high impedance (high voltage, low current) at the output of the supply unit, such as indicated by the point A along the abscissa in FIG. 2. This corresponds to a desired power output as represented by the point B along the ordinate axis. The output of the memory 40 as determined by the digital signals on lines 36, 37, 41 and 42 is read out on line 53 to control the power supply unit 1 to produce a power level of B watts. As the hand-held electrode 20 is brought into contact with tissue, the impedance will drop, such as to a value represented by the point C along the abscissa. This changes the current and voltage output feedback signals, thereby changing the address signal and causing a different storage location in the memory 40 to be addressed. The information contained in this location will be representative of a different point along the same power curve and will therefore, in general be representative of a different power level D.

If the surgeon should select a different mode during a surgical technique, this produces a different signal on line 42 thereby causing a different storage location to be addressed in the EPROM 142 which will contain information about the power level of a different family of power curves.

The EPROM 142 may be pluggable so as to be readily changeable so that, for example, a family of different apparatus with different power curve characteristics could be produced readily with other components common. The memory 40 may be adjustable by the user so that he can set the desired shape of the power curve. In this respect, the apparatus could be provided with a bank of vertical slider controls arranged side-by-side so that each can be set at the desired power level for a respective value of impedance. Some form of processor will be required to convert the settings of the controls in a form suitable for modifying the memory.

The apparatus employs a feedback loop 50 by which a sample of the measured voltage is supplied from the A-D converter 35 via lines 36 and 51 to one input of a comparator or adder 52 in the power control unit 11. The other input to the adder 52 is representative of the required voltage as supplied by the output of the memory 40 via line 53. The two inputs to the adder 52 therefore constitute the measured voltage and the negative value of the desired voltage respectively. The adder 52 has two outputs shown as lines 54 and 55. The output line 54 is supplied to a digital-to-analog converter 56 and is in respect of the magnitude of the sum of the inputs on lines 51 and 53, that is, the difference between the measured and desired values of the voltage. The other output on line 55 constitutes a sign bit to indicate which of the inputs is greater, that is, whether the actual voltage exceeds the desired voltage and should therefore be reduced, or whether the actual voltage is less than the desired voltage and should therefore be increased. Because the adder 52 operates with digital inputs, there is no error in the comparison. The output on line 55 is supplied to an input of the r.f. amplifier 10. The D-A converter 56 provides another input to the r.f. amplifier 10, via an analog amplifier 57 which is in the form of an error signal representative of the magnitude of the change required in the voltage at the output of the r.f. amplifier 10. This error signal is also supplied to a system monitor unit 58 which is connected to an alarm 59.

The adder 52, converter 56 and amplifier 57 may be regarded as part of a power control unit 11 which also includes a pulse pattern generator 60 that provides an input to the r.f. amplifier 10 to control the pulse pattern produced.

In operation, if the output voltage of the r.f. amplifier 10 should fall below the desired level established by the setting of the power level switch 43 and the power curve selected by the mode switch 44, the adder 52 will produce an "increase power" signal on line 55 and a signal on line 54 which indicates the magnitude of the change in input voltage to the amplifier 10 such that its output voltage will be increased to the desired level. As the output voltage approaches the desired level, the magnitude of the error will decrease and the output will exhibit a damped response dependent on the time constants within the r.f. amplifier 10. When the measured voltage equals the desired voltage the error signal will be zero and the system will be stable.

It will be appreciated that, instead of providing separate magnitude and increase/decrease signals, a bipolar signal could be provided indicating the increase or decrease in power level inherently.

It is also possible to program the memory 40 differently for individual apparatus in response to automatic testing of the apparatus or components so that the power curves are the same from apparatus to apparatus despite differences in the components of the apparatus.

The multi-bit input address signal to the memory 40 could also include an address from a timing unit so that different locations in the memory are addressed at different times. This facility could be used to control the way in which the output power is varied with change in impedance. For example, it could be used to control the rate of increase of power.

Instead of converting the voltage and current signals on lines 36 and 37 to an impedance signal before addressing the look-up table in the EPROM 142, it would be possible to address the EPROM directly with the five-bit current and voltage signals. In effect, this would result in a ten-bit impedance signal instead of the eight-bit impedance signal derived by use of the EPROM 140.

Alternatively, a similar arrangement could be utilized in which a current feedback is employed, rather than voltage.

Figure 4:
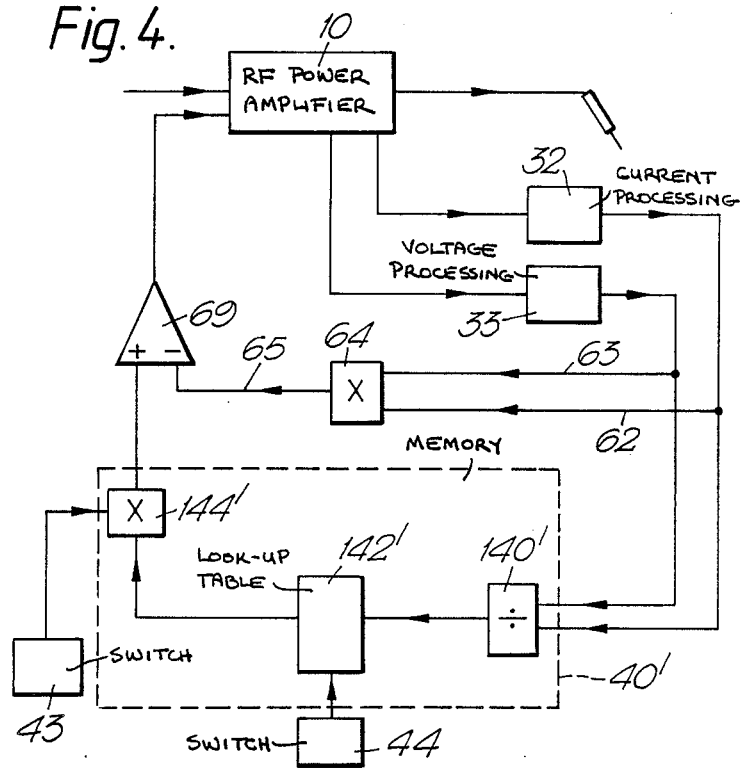
FIG. 4 shows schematically a modification of the apparatus.

A further alternative arrangement is illustrated in FIG. 4 which is similar in construction to the arrangement of FIG. 1 except that, instead of a voltage feedback loop, a power feedback loop is employed. The power feedback loop is constituted by taking samples of both the current and voltage outputs from the current and voltage processing units 32 and 33 respectively on lines 62 and 63. These are supplied to a multiplier unit 64 which produces an output on line 65 representative of the power output of the r.f. amplifier 10. In this arrangement the memory 40' contains a look-up table 142' of values of the required power at full power setting. The look-up table 142', is addressed in accordance with the mode/power curve selected by the switch 44 and the actual value of tissue impedance derived by a unit 140' which divides the current and voltage outputs from the units 32 and 33. The required power at full setting is converted into the actual required power by means of a multiplier unit 144' which multiplies the desired power level as set by the switch 43 with the output from the look-up table 142'. The output of the multiplier unit 144' is compared in a differential amplifier 69 with the actual measured power on line 65 to produce an error control voltage that is supplied to the input of the r.f. amplifier 10. If the actual power should fall below the desired power level, the input to the amplifier 10 causes it to increase its output voltage and hence increase the output power. Similarly, if the power level should rise above the desired level, the input to the amplifier causes it to decrease its output voltage and hence decrease the output power.

Various elements of this apparatus can operate digitally. For example, the multiplier 64 may be provided by another look-up table, and the differential amplifier 69 may include a subtractor followed by a digital-to-analog converter.

It is not essential for the apparatus to have any feedback signal. Instead, the look-up table could contain, at its different storage locations, a representation of the input voltage needed to be supplied to the r.f. amplifier 10 to produce the desired power output. However, by using an error signal derived from feedback as in the arrangements described above, the apparatus is independent of the performance of the r. f. amplifier. Furthermore, monitoring of the error signal produces a way of determining if the apparatus is functioning correctly. An excessive error signal indicates that there may be a malfunction in the apparatus and causes the alarm 59 to be activated.

The invention enables apparatus of great flexibility to be provided in which the ideal power curve is provided consistently for different surgical modes and power levels or other performance characteristics.

The invention is not restricted to use with electrosurgery but could be used in other applications where it is desired to control the power level of electrical apparatus.

What I claim is:

1. Electrical power control apparatus comprising: a power supply unit, said power supply unit being arranged to deliver an alternating power output signal; store means including a plurality of storage locations, each of said storage locations containing information for use in providing an input signal, means for supplying said input signal to said power supply unit such as to control the level of the power output signal in accordance therewith; means for deriving a first digital signal representative of the voltage and current of the output signal; means for deriving a second digital signal representative of a performance characteristic of the apparatus, wherein the first and second digital signals together define the location of one of said storage locations such that as the output voltage, current or performance characteristic changes a different one of said storage locations is addressed and said input signal is varied accordingly to control said output signal.

2. Electrical power control apparatus according to claim 1, including a manually settable switch and means connecting said switch with said store means such that performance characteristic is set by said switch.

3. Electrical power control apparatus according to claim 1, wherein said first digital signal is an impedance signal.

4. Electrical power control apparatus according to claim 3, including second store means including a plurality of storage locations, each of the storage locations in said second store means containing information representative of said impedance signal, means for deriving a digital signal representative of the voltage of the output signal, means for deriving a digital signal representative of the current of the output signal, and wherein the storage locations in said second store means are addressed by the digital signal representative of voltage and the digital signal representative of current.

5. Electrical power control apparatus according to claim 1, wherein said second digital signal is representative of the shape of a desired curve of power against impedance.

6. Electrical power control apparatus according to claim 1, including comparator means, said comparator means having two inputs, means for deriving a feedback signal from the output of said power supply unit, means for supplying said feedback signal to one input of the comparator means, and means for supplying an output from said store means to the other input of the comparator means, said comparator means comparing the signals at its two inputs and deriving input signal to the power supply unit.

7. Electrical power control apparatus according to claim 6, including alarm means, and means connecting comparator means to said alarm means, and wherein said alarm means is arranged to provide an alarm signal when the output of the comparator means exceeds a predetermined amount.

8. Electrical power control apparatus according to claim 1, including a manually settable power level switch, and wherein input signal to the power supply unit is adjustable according to the desired power level as indicated by power level switch.

9. Electrical power control apparatus according to claim 8, wherein the storage locations in said store means contain representations of input signal at full power, and wherein apparatus includes means for modifying representations at full power according to the desired power level as indicated by the power level switch.

10. Electrosurgery apparatus comprising: an r.f. power supply unit, said power supply unit being arranged to deliver an r.f. power output signal at a level that is controlled by an input signal to the power supply unit; a patient electrode; means connecting the patient electrode to an output of the power supply unit; means deriving a digital signal representative of the voltage of the output signal; means deriving a digital signal representative of the current of the output signal; a store, said store containing a plurality of storage locations each of which contain information representative of an impedance signal; means for addressing said store with the digital signals representative of voltage and current so as to identify the location of one of said storage locations and read out a digital impedance signal therefrom; a manually settable switch, said switch being settable to derive a digital signal representative of the shape of a desired curve of power against impedance; a further store, said further store containing a plurality of storage locations each of which contains information for use in providing said input signal; means for addressing said further store with said digital impedance signal and the digital signal derived from said switch so as to identify the location of one of said storage locations in said further store and read out information contained therein; and means for deriving said input signal for the power supply unit from said information.

11. A method of controlling the electrical power delivered by a power supply unit of the kind that is responsive to an input signal at an input thereof to produce an alternating power output signal, including the steps of: deriving a first digital signal representative of the voltage and current of the output signal; deriving a second digital signal representative of a performance characteristic; supplying the first and second digital signals to identify one of a plurality of storage locations in store means; deriving a signal from information contained in said storage location; and supplying the signal derived from said information to the input of said power supply unit to control the output of said power supply unit.

* * * * *